United States Patent [19]

Van der Ploeg et al.

[11] Patent Number: 4,908,308

[45] Date of Patent: Mar. 13, 1990

[54] METHOD FOR DETECTING ANIMAL-INFECTIVE PROTOZOA IN VITRO AND A METHOD FOR DETECTING AGENTS WHICH BLOCK THE DIFFERENTIATION THEREOF

[75] Inventors: Lex H. T. Van der Ploeg; Suzanne H. Giannini; Charles R. Cantor, all of New York, N.Y.

[73] Assignee: The Trustees of Columbia University in the City of New York, New York, N.Y.

[21] Appl. No.: 746,282

[22] Filed: Jun. 19, 1985

[51] Int. Cl.[4] .......................... C12Q 1/68; C12Q 1/18; C12Q 1/04; C12Q 1/06

[52] U.S. Cl. .......................................... 435/6; 435/32; 435/34; 435/39

[58] Field of Search ................... 435/6, 29, 32, 34, 35, 435/39, 91, 245, 258, 947, 820

[56] References Cited

U.S. PATENT DOCUMENTS 4,556,643 12/1985 Paau et al. ............................ 435/34

OTHER PUBLICATIONS

Hunter et al., (1984), Biochemical and Biophysical Research Communications, vol. 125, No. 2, pp. 755–760.
Schlesinger et al., (1982), Heat Shock from Bacteria to //// Cold SPring Harber Laboratory, pp. 2–7, 419–422.
Zimmerman et al., (1983), Cell, vol. 32, pp. 1161–1170.
Fong et al., (1984), Proceedings of the National Academy of Science, U.S.A., vol. 81, pp. 5782–5786.
Schmur et al., (1983), Chemical Abstracts, vol. 99, No. 15, p. 370, Item No. 119186z.

*Primary Examiner*—Randall E. Deck
*Attorney, Agent, or Firm*—John P. White

[57] ABSTRACT

This invention concerns a method for identifying in vitro an animal-infective form of a parasitic protozoan which comprises recovering total mRNA from the protozoan and detecting in the mRNA so recovered the presence of a mRNA transcript encoding a heat shock protein associated with animal-infective parasitic protozoans, which transcript is present only in the animal-infective form of the protozoan, or quantitatively determining in the mRNA so recovered the number of a mRNA transcript encoding a heat shock protein associated with animal-infective parasitic protozoans, which transcript is present in increased number only in the animal-infective form of the parasitic protozoan.

This invention also concerns a method for identifying an agent capable of blocking the formation of the animal-infective form of a parasitic protozoan.

48 Claims, No Drawings

METHOD FOR DETECTING ANIMAL-INFECTIVE PROTOZOA IN VITRO AND A METHOD FOR DETECTING AGENTS WHICH BLOCK THE DIFFERENTIATION THEREOF

BACKGROUND OF THE INVENTION

Throughout this application various publications are referenced by the names of the authors and the year of publication within parentheses. Full citations for these publications may be found at the end of the specification immediately preceding the claims. The disclosures of these publications in their entireties are hereby incorporated by reference into this application in order to more fully describe the state of the art to which this invention pertains.

Heat shock genes are activated in the response of a cell to stress, such as an increase in temperature or exposure to inhibitors of oxidative phosphorylation (1). The heat shock response involves the immediate activation of several heat shock genes, resulting in extensive synthesis of several heat shock proteins (Hsp's), plus a rapid decrease of transcription of most other genes and a cessation of most other protein synthesis (for review refs. 1, 2). In many organisms heat shock related genes are expressed during cell development For instance heat shock genes are expressed specifically in mice during early embryogenesis (3), in erythropoesis (4), and at sporulation in yeast (5). The role of the heat shock gene response in these cases is unclear but t indicates that heat shock proteins, which have a nuclear location (6, 7) may be involved in differentiation.

Many parasitic protozoa have life cycles that involve an insect vector and a mammalian host. Adaption of the protozoa to either of its hosts involves differentiation accompanied by extensive morphological alterations, often including a sexual life cycle in the insect vector and a switch from oxidative phosphorylation in the insect to anaerobic respiration in the mammalian host (8). *Trypanosoma brucei* in addition has been shown to lose its protective cell surface coat when entering the fly gut where it differentiates into the non-infective procyclic trypanosome (9, 10). This cell surface coat is re-expressed in the infective metacyclic trypanosomes that are found in the insect salivary glands (10). Here we show that differentiation of the Kinetoplastid protozoa *Trypanosoma brucei* and *Leishmania tropica major*, involves a heat shock response. Insect vectors like the sandfly and the tsetse fly (transmitting *L.t. major* and *T. brucei*, respectively) are restricted to habitats with a very narrow temperature range from 22° C. to 28° C. (11, 12). In vivo, transfer of the parasite from its non-temperature regulated (poikilothermic) insect vector to the homeothermic mammalian host will therefore trigger this heat shock response. In vitro this response can be mimicked by a temperature increase (25° C. to 37° C.) which results in differentiation similar to that which occurs in vivo.

SUMMARY OF THE INVENTION

This invention concerns a method for identifying in vitro an animal-infective (i.e. mammalian-infective) form of a parasitic protozoan which comprises recovering total mRNA from the protozoan and detecting in the mRNA so recovered the presence of a mRNA transcript encoding a heat shock protein associated with animal-infective parasitic protozoans, which transcript is present only in the animal-infective form of the protozoan, or quantitatively determining in the mRNA so recovered the number of a mRNA transcript encoding a heat shock protein associated with animal-infective parasitic protozoans, which transcript is present in increased number only in the animal-infective form of the parasitic protozoan. In a presently preferred embodiment, prior to recovering mRNA from the protozoan the protozoan is subjected in vitro to a temperature of about 37° C. for a sufficient time to cause the protozoan to differentiate to the animal-infective form. Parasitic protozoans may be of the genus Leishmania or the genus Trypanosoma, as well as various other varieties of protozoa.

This invention further concerns a method for the detection of mRNA transcripts encoding heat shock proteins associated with animal-infective (i.e. mammalian-infective) parasitic protozoans which transcripts are present only in the animal-infective form of the protozoan which comprises contacting the total mRNA recovered from the protozoan under hybridizing conditions with a detectable oligonucleotide which is complementary to at least a portion of the mRNA transcripts and detecting the formation of hybridization complexes between the mRNA transcripts and the detectable oligonucleotide and thereby detecting the presence of mRNA transcripts encoding heat shock proteins associated with animal-infective parasitic protozoans. Also disclosed is a method for the quantitative determination of mRNA transcripts encoding heat shock proteins associated with animal-infective parasitic protozoans, which transcripts are present in increased numbers only in the animal-infective form of the protozoan, which comprises contacting the total mRNA recovered from the protozoan under hybridizing condtions with a detectable oligonucleotide which is complementary to at least a portion of the mRNA transcripts and quantitatively determining the formation of hybridization complexes between the mRNA transcripts and the detectable oligonucleotide and thereby detecting the increase in number of mRNA transcripts encoding heat shock proteins associated with animal-infective parasitic protozoans.

In a presently preferred embodiment the detectable oligonucleotide comprises at least a portion of a Drosophila heat shock gene, preferably Hsp 83 or Hsp 70. The detectable oligonucleotide may be radioactively labeled and may be detected using a variety of methods, such as gel electrophoresis or scintillation counting.

Finally, the invention concerns a method for identifying an agent capable of blocking the formation of the animal-infective form of a parasitic protozoan which comprises in vitro separately subjecting a non-infective form of the protozoan in the presence of different amounts of the agent to a temperature of about 37° C. for a sufficient time to cause the protozoan to differentiate to the animal-infective form, recovering total mRNA from the protozoan and detecting or quantitatively determining in the mRNA so recovered a mRNA transcript encoding a heat shock protein associated with animal-infective parasitic protozoans, which transcript is present or increased in number only in the animal-infective form of the protozoan, the absence of the mRNA transcript or lack of increase in the number thereof indicating that the agent has blocked the formation of the animal-infective form so as to thereby identify the agent.

The presently preferred detectable oligonucleotide comprises at least a portion of a Drosophila heat shock gene, preferably Hsp 83 or Hsp 70. The detectable oligonucleotide may be radioactively labeled and may be detected using a variety of methods, such as gel electrophoresis or scintillation counting.

DETAILED DESCRIPTION OF THE INVENTION

A method is disclosed for identifying in vitro an animal-infective form of a parasitic protozoan which comprises recovering total mRNA from the protozoan and detecting in the mRNA so recovered the presence of a mRNA transcript encoding a heat shock protein associated with animal-infective parasitic protozoans, which transcript is present only in the animal-infective form of the protozoan, or quantitatively determining in the mRNA so recovered the number of a mRNA transcript is present in increased number only in the animal-infective form of the parasitic protozoan.

In a presently preferred embodiment, prior to recovering mRNA from the protozoan, the protozoan is subjected in vitro to a temperature of about 37° C. for a sufficient time to cause the protozoan to differentiate to the animal-infective form.

A presently preferred parasitic protozoan is of the genus Leishmania or the genus Trypanosoma; e.g., *L. tropica major, L. brasiliensis, L. peruviana, L. mexicana, L. donovani, L. chagasi, L. enviettii, L. hertigi, L. adleri, T. brucei, T. gambiense, T. rhodesiense, T. lewisi* or *T. rangeli*, but may also be a protozoan of the genera Coccidia, Babesia, Theileria, Plasmodium or Giardia, as well as other genera.

In a presently preferred embodiment, the detection of mRNA transcripts encoding heat shock proteins associated with animal-infective parasitic protozoans, which transcripts are present only in the animal-infective form of the protozoan, comprises contacting the total mRNA recovered from the protozoan under hybridizing conditions with a detectable oligonucleotide which is complementary to at least a portion of the mRNA transcripts and detecting the formation of hybridization complexes between the mRNA transcripts and the detectable oligonucleotide and thereby detecting the presence of mRNA transcripts encoding heat shock proteins associated with animal-infective parasitic protozoans.

In a preferred embodiment, the detectable oligonucleotide comprises at least a portion of the DNA from Drosophila which encodes a Drosophila heat shock protein; e g. a portion of the DNA encoding Hsp 83 or Hsp 70, although DNA encoding heat shock genes from other organisms, e.g., murine heat shock genes or yeast heat shock genes, may also be used.

In a presently preferred embodiment, the detectable oligonucleotide is radioactively labeled, a procedure known to those skilled in the art, although other means of labeling the oligonucleotides may be used.

In a presently preferred embodiment, the detection of the formation of hybridization complexes comprises gel electrophoresis; e.g., total RNA from the protozoan is treated with DNase I, separated by electrophoresis in a 1.5% agarose gel and transferred to nitrocellulose filters, where it is then hybridized with the labeled oligonucleotide and the hybridization complexes are detected by autoradiography. Alternatively, the hybridization complexes may be detected by suspending the complexes in scintillation flour and then quantifying the radioactive decay from the complexes in a scintillation counter. Further, the mRNA transcripts may be detected or quantitatively determined by preparing monoclonal antibodies to the transcripts and then contacting the monoclonal antibodies so prepared with the total protozoan RNA and detecting the monoclonal antibody - mRNA complexes formed thereby.

In a presently preferred embodiment, the quantitative determination of mRNA transcripts encoding heat shock proteins associated with animal-infective parasitic protozoans, which transcripts are present in increased numbers only in the animal-infective form of the protozoan, comprises contacting the total mRNA recovered from the protozoan under hybridizing conditions with detectable oligonucleotide which is complementary to at least a portion of the mRNA transcripts and quantitatively determining the formation of hybridization complexes between the mRNA transcripts and the detectable oligonucleotide and thereby detecting the increase in number of mRNA transcripts encoding heat shock proteins associated with animal-infective parasitic protozoans.

In a presently preferred embodiment, the detectable oligonucleotide comprises at least a portion of the DNA from Drosophila which encodes a Drosophila heat shock protein; e.g. a portion of the DNA encoding Hsp 83 or Hsp 70, although DNA encoding heat shock genes from other organisms, e.g., murine heat shock genes or yeast heat shock genes, may also be used.

In a presently preferred embodiment, the detectable oligonucleotide is radioactively labeled, a procedure known to those skilled in the art, although other means of labeling the oligonucleotides may be used.

In a presently preferred embodiment, the detection of the formation of hybridization complexes comprises gel electrophoresis; e.g., total RNA from the protozoan is treated with DNase I, separated by electrophoresis in a 1.5% agarose gel and transferred to nitrocellulose filters, where it is then hybridized with the labeled oligonucleotide and the hybridization complexes are detected by autoradiography. Alternatively, the hybridization complexes may be detected by suspending the complexes in scintillation flour and then quantifying the radioactive decay from the complexes in a scintillation counter. Further the mRNA transcripts may be detected or quantitatively determined by preparing monoclonal antibodies to the transcripts and then contacting the monoclonal antibodies so prepared with total protozoan RNA and detecting the monoclonal antibody - mRNA complexes formed thereby.

Additionally, a method is disclosed for identifying an agent capable of blocking the formation of the animal-infective form of a parasitic protozoan which comprises in vitro separately subjecting a non-infective form of the protozoan in the presence of different amounts of the agent to a temperature of about 37° C. for a sufficient time to cause the protozoan to differentiate to the animal-infective form, recovering total mRNA from the protozoan and detecting in the mRNA so recovered a mRNA transcript encoding a heat shock protein associated with animal-infective parasitic protozoans, which transcript is present only in the animal-infective form of the protozoan, the absence of the mRNA transcript indicating that the agent has blocked the formation of the animal-infective form so as to thereby identify the agent.

In a presently preferred embodiments, the parasitic protozoan is of the genus Leishmania, Trypanosoma, Coccidia, Babesia, Theileria, Plasmodium or Giardia, although other varieties may also be used.

In a presently preferred embodiment, the in vitro separately subjecting a non-infective form of the protozoan to a temperature of about 37° C. for a sufficient time comprises growing the low temperature insect stage, e.g., the promastigote form when the protozoan is a Leishmania or a procyclic or metacyclic form when the protozoan is a Trypanosoma, at a temperature of about 37° C. for about five days, or until the protozoan differentiates into the animal-infective form, e.g., an amastigote when the protozoan is a Leishmania or a trypomastigote when the protozoan is a Trypanosoma.

In a presently preferred embodiment, the detection of mRNA transcripts encoding heat shock proteins associated with animal-infective parasitic protozoans which transcripts are present only in the animal-infective form of the protozoan, comprises contacting the total mRNA recovered from the protozoan under hybridizing conditions with a detectable oligonucleotide which is complementary to at least a portion of the mRNA transcripts and detecting the formation of hybridization complexes between the mRNA transcripts and the detectable oligonucleotide and thereby detecting the presence of an mRNA transcript encoding heat shock proteins associated with animal-infective parasitic protozoans.

In a presently preferred embodiment, the detectable oligonucleotide comprises at least a portion of the DNA from Drosophila which encodes a Drosophila heat shock protein; e.g., a portion of the DNA encoding Hsp 83 or Hsp 70, although DNA encoding heat shock genes from other organisms, e.g., murine heat shock genes or yeast heat shock genes, may also be used.

In a presently preferred embodiment, the detectable oligonucleotide is radioactively labelled, a procedure known to those skilled in the art, although other methods of labeling the oligonucleotides may be used.

In a presently preferred embodiment the detection of the formation of hybridization complexes comprises gel electrophoresis; e.g., total RNA from the protozoan is treated with DNase I, separated by electrophoresis in a 1.5% agarose gel and transferred to nitrocellulose filters, where it is then hybridized with the labeled oligonucleotide and the hybridization complexes are detected by autoradiography. Alternatively, the hybridization complexes may be detected by suspending the complexes in scintillation flour and then quantifying the radioactive decay from the complexes in a scintillation counter. Further, the mRNA transcripts may be detected or quantitatively determined by preparing monoclonal antibodies to the transcripts and then contacting the monoclonal antibodies so prepared with the total protozoan RNA and detecting the monoclonal antibody - mRNA complexes formed thereby.

Finally, a method is disclosed for identifying an agent capable of blocking the formation of the animal-infective form of a parasitic protozoan which comprises in vitro separately subjecting a non-infective form of the protozoan in the presence of different amounts of the agent to a temperature of about 37° C. for a sufficient time to cause the protozoan to differentiate to the animal-infective form, recovering total mRNA from the protozoan and quantitatively determining in the mRNA so recovered a mRNA transcript encoding a heat shock protein associated with animal-infective parasite protozoans, which transcript is increased in number only in the animal-infective form of the protozoan, the absence of an increase in the number of the mRNA transcript indicating that the agent has blocked the formation of the animal-infective form so as to thereby identify the agent.

In a presently preferred embodiment, the parasitic protozoan is of the genus Leishmania, Trypanosoma, Coccidia, Babesia, Theileria, Plasmodium or Giardia, although other varieties may also be used.

In a presently preferred embodiment, the in vitro separately subjecting a non-infective form of the protozoan to a temperature of about 37° C. for a sufficient time comprises growing the low temperature insect stage, e.g., the promastigote form when the protozoan is a Leishmania or a procyclic or metacyclic form when the protozoan is a Trypanosoma, at a temperature of about 37° C. for about five days, or until the protozoan differentiates in the animal-infective form, e.g., an amastigote when the protozoan is a Leishmania or a trypomastigote when the protozoan is a Trypanosoma.

In a presently preferred embodiment, the quantitative determination of mRNA transcripts encoding heat shock proteins associated with animal-infective parasitic protozoans which transcripts are increased in number only in the animal-infective form of the protozoan which comprises contacting the total mRNA recovered from the protozoan under hybridizing conditions with a detectable oligonucleotide which is complementary to at least a portion of the mRNA transcripts and detecting the formation of hybridization complexes between the mRNA transcripts and the detectable oligonucleotide and thereby detecting increase in number of the mRNA transcripts encoding heat shock proteins associated with animal-infective parasitic protozoans.

In a presently preferred embodiment, the detectable oligonucleotide comprises at least a portion of the DNA from Drosophila which encodes a Drosophila heat shock protein; e.g., a portion of the DNA encoding Hsp 83 or Hsp 70, although DNA encoding heat shock genes from other organisms, e.g., murine heat shock genes or yeast heat shock genes, may also be used.

In a presently preferred embodiment, the detectable oligonucleotide is radioactively labelled, a procedure known to those skilled in the art, although other methods of labeling the oligonucleotides may be used.

In a presently preferred embodiment the detection of the formation of hybridization complexes comprises gel electrophoresis; e.g., total RNA from the protozoan is treated with DNase I, separated by electrophoresis in a 1.5% agarose gel and transferred to nitrocellulose filters, where it is then hybridized with the labeled oligonucleotide and the hybridization complexes are detected by autoradiography. Alternatively, the hybridization complexes may be detected by suspending the complexes in scintillation flour and then quantifying the radioactive decay from the complexes in a scintillation counter. Further, the mRNA transcripts may be detected or quantitatively determined by preparing monoclonal antibodies to the transcripts and then contacting the monoclonal antibodies so prepared with the total protozoan RNA and detecting the monoclonal antibody - mRNA complexes formed thereby.

EXPERIMENTAL DETAILS

Sequences related to the Drosophila Hsp 70 (13) and HsP 83 (14) heat shock genes can be detected in nuclear DNA of T.brucei and L.t.major at relaxed stringency hybridization conditions. In this experiment, nuclear DNA of T.brucei stock 427 (21) and L.t.major (22) was prepared as described in reference (23). Nuclear DNA was digested with Hind III and size separated in a 0.7% agarose gel, transferred to nitrocellulose filters and hybridized with the Drosophila Hsp 70 (0.2 kb Bam HI -Sal I fragment) and Hsp 83 (2.9 kb Hae III fragments derived from clone 244) gene probes at 65° C. and 3×SSC stringency of hybridization as described in reference (23). Since yeast (15, Petko and Lindquist, unpublished) or Drosophila derived 5'-or 3'- half Hsp gene probes recognize the same Hsp 70 or Hsp 83 specific restriction enzyme fragments, the hybridizations are not due to fortuitous homology. In both *T.brucei* and *L.t.major* one Hind III fragment is determined with the Drosophila Hsp 83 gene probe. Since *T.brucei* and *L.t. major* nuclear DNA digested with Hae II shows at least 10 hybridizing fragments (0.5–6 kb in length) with the Hsp 83 probe, a family of related genes may be closely linked in their genomes. With the Drosophila Hsp 70 probe two strong and several weak hybridizing fragments are detected in *T.brucei* nuclear DNA. Only one large (20 kb) strong hybridizing fragment is seen in *L.t. major* nuclear DNA to which in addition numerous smaller fragments hybridize. Heat shock sequences related to the class or small genes (Hsp 24; refs. 1. 2) could not be detected.

The heat shock related sequences are transcribed in both *T.brucei* and *L.t.major* in *T.brucei* bloodstream-derived trypanosomes (trypomastigotes) expression of both the Hsp 70 and Hsp 83 related genes is found. For the detection of Hsp transcripts we used RNA prepared from total rat blood infected with trypanosomes (24, 25). These RNA preparations are made directly after bleeding the rat in order to minimize loss of transcripts that may occur during the normal lengthy, low temperature, trypanosome purification. We used the Drosophila Hsp 70 and Hsp 83 genes and the *T.brucei* Hsp 70 related gene as probes on northern blots of total mRNA (26). The Drosophila Hsp 83 probe hybridizes to a transcript of 2600 nucleotides (nt); both the Drosophila and the *T.brucei* Hsp 70 probes hybridize with a transcript of 2300 nt in bloodstream RNA while RNA prepared from uninfected rat blood shows no hybridization at all with the Hsp 70 and Hsp 83 probes. The mRNA levels are considerably higher then those seen in the low temperature (28° C.) culture-form procyclic trypanosomes for both the Hsp 70 and Hsp 83 transcripts. The difference was quantitated by scanning the autoradiograms and comparing the hybridization signals to that of tubulin (27), which is twofold weaker in procylcic trypanosomes. Relative to tubulin, procylcic trypanosomes show a 30-fold decrease in the Hsp mRNA compared to the bloodstream form. However, the twofold difference between the tubulin hybridization signal in trypomastigotes and procyclic trypanosomes must reflect a true decrease of tubulin mRNA levels in the procyclic trypanosome because the RNA concentrations have been carefully monitored and tubulin does not hybridize under these conditions with RNA prepared from uninfected rat blood. Furthermore the trypomastigote RNA was prepared from total infected rat blood and will be contaminated with rat RNA. Thus, the 30-fold Hsp mRNA difference will be a lower limit and the true difference is likely to be at least a 100-fold. *Leishmania tropica major* has a life cycle with an insect vector, the sandfly, and a intracellular stage in the macrophages of a mammalian host (16). In *L.t.major*, mRNA levels of the Hsp 70 and Hsp 83 related genes show both quantitative and absolute differences between promastigotes (insect stage) and amastigotes (mammalian stage). With an Hsp 70 gene probe, four transcripts are detected in lesion derived amastigotes. Only one of these, a 1900 nt transcript, comigrates with the 25° C. culture-form promastigote transcripts. The transcription pattern of the Hsp 83 related heat shock genes is also different when compared between promastigotes and lesion derived amastigotes. The two most abundant of the four amastigote transcripts comigrate with the promastigote Hsp RNA's. The two additional minor transcripts are detected only in the lesion amastigotes. These *L.t.major* mRNAs are retained by oligo dT selection. Drosophila heat shock mRNAs however have very short poly-A tails and cannot be retained on oligo dT columns. We therefore do not know whether the *L.t. major* transcripts have an A rich leader on the mRNA or a poly-A tail.

If the differentiation of the parasite from the insect to the bloodstream-form is mainly the result of a heat shock response, it should be possible to induce differentiation by growing the low temperature insect stage at elevated temperatures. We performed this experiment on *L.t.major* culture promastigotes and compared the morphology and RNA levels of promastigotes (25° C.) with those of a promastigote culture grown at 37° C. for 5 days and with those of lesion derived amastigotes. The 25° C. culture-form promastigotes are long slender cells while the amastigotes from lesions and promastigotes from 37° C. cultures are small round cells (as has recently also been indicated for *L.mexicana*, 29). Thus the temperature shift produces an apparently complete morphological transformation of the promastigote. On the basis of three criteria we conclude the transformation to be complete. First, using serum prepared against lesion amastigotes, the high temperature promastigotes show a 10-fold increase in antigenicity in a dot ELISA (22) compared to the low temperature promastigotes. The high temperature promastigotes remained fully viable and infective to Balb/c mice. Second, RNA prepared from these culture-form amastigotes was compared with the RNA of promastigotes and lesion amastigotes. Both the patters of hybridization with the Hsp 70 and Hsp 83 heat shock genes for the lesion amastigotes and the culture-form amastigotes are almost identical. Third, a characteristic pattern of α and β tubulin gene expression is known to result from the differentiation of promastigotes to amastigotes in *L. enriettii* (17). We examined *L.t. major* promastigotes, lesion amastigotes and culture-form amastigotes to see if a temperature shift would yield a similar characteristic pattern of tubulin transcripts. Following heat shock, the mRNA's hybridizing with the tubulin gene probe are identical in lesion and culture-form amastigotes except for the level of expression of the 2400 nt transcript, which is less abundant in culture-form amastigotes. The loss of the 3000 nt transcript together with the smear of hybridization at 2000 nt following the temperature shift are the most obvious differences between promastigotes and amastigotes. The new transcript is detected at 2200 nt which was not present in promastigotes. Tubulin genes in Leishmania may therefore be under heat shock control. Thus these results show that the temperature treated culture-form promastigote differentiates into an amastigote which we refer to as a "culture-form amastigote".

As has previously been shown in Drosophila (18–19) heat shock genes do not respond only to heat stress. In *T.brucei* induction of heat shock gene expression could be retained at 22° C. when trypanosomes were grown under conditions where they remained infective to laboratory animals and thus did not differentiate to the procyclic insect stage. For this purpose bloodstream trypanosomes were adapted to culture with rat embryo fibroblast feeder layer cells (20). These culture-form trypomastigotes (division time 12 hours at 34° C.) were grown at both 22° C. and 34° C. for three days. The heat shock gene transcription pattern and infectivity to mice was then tested. In a hybridization of RNA made from both cultures with the Hsp 83 and tubulin gene probes, the amount of heat shock gene transcript for both the Hsp 70 and the Hsp 83 genes is identical in both the 22° C. and 34° C. cultures. Also the levels of expression of Hsp mRNAs in the cultures at both temperatures is identical to that of bloodstream trypanosomes (deduced by comparison of tubulin mRNA hybridization signals with these heat shock gene transcripts and those in bloodstream trypomastigotes). Since both cultures retained infectivity to mice it is clear that these trypanosomes did not differentiate to procyclic stages following the temperature decrease. This complex pattern of heat shock gene behavior indicates that growth conditions can mimic heat shock responses. The high level of expression of several of the *L.t. major* heat shock gene transcripts in promastigotes and these *T. brucei* transcripts may reflect this.

The results show that a heat shock response exists in parasitic protozoa that naturally shuttle between a non-temperature regulated (22° C. to 28° C. (11, 12) insect vector and a temperature regulated (37° C.) mammalian host. While a heat shock response in other eukaryotes serves to shut down overall protein synthesis the response in these parasitic protozoa does not seem to interfere with cell activity. Trypanosomes and Leishmania divide normally at the higher temperature and are therefore not in the quiescent state of heat shocked cells. The heat shock genes are therefore likely to have a different function in these protozoa. In vitro temperature shift experiments with *L.t. major* completely support the hypothesis that differentiation results from a temperature shift. Thus it is possible that the heat shock genes have a regulatory function in the differentiation process. However we do not know at what level regulation of heat shock mRNA occurs. The elevated levels of heat shock transcripts in *T. brucei* and the newly detected transcripts in *L.t. major* may arise from enhanced transcription of their heat shock genes as is the case for heat shock genes in other organisms. Furthermore, since the experiments show that the differentially expressed tubulin genes may be under this heat shock control, the temperature shift could start a development program, by enhancing Hsp transcription, which results in adaptation to life in the mammalian host tissues. Our finding of a heat shock response in differentiating protozoa suggests a role for the heat shock genes in eukaryotic cell differentiation.

It is interesting to note the effect of stimuli that mimic a heat shock response in Drosophila and the effect of a heat shock response in *T.brucei* and *L.t. major*. Several drugs that affect mitochodrial respiration in Drosophila mimic a heat shock response at low temperature growth conditions (18,19); most of these interfere with oxidative phosphorylation. Since both *T.brucei* and *L.t. major* rely solely on glycolysis for their energy demands and mitochondrial respiration is repressed when present in the mammal (8), this development partway may be under control of the activated heat shock genes.

REFERENCES

1. Ashburner, M. and Bonner, J. J., Cell, 17, 241–254 (1979).
2. Schlesinger, M. J., Ashburner, M. and Tissieres, A., Heat shock from bacteria to man. Cold Spring Harbor Laboratory (1982).
3. Bensaude, O., Babinet, C., Morange, M. and Jacob, F., Nature, 305, 331–333, (1983).
4. Mandaleshwar, K. S. and Yu, J., Nature, 309, 631–633, (1984).
5. Kurtz, S. and Lindquist, S., Proc. Natl. Acad. Sci., in press (1984).
6. Velazquez, J. M., Didomenico, B. J. and Lindquist, S., Cell, 20, 679–689 (1980).
7. Vincent, M. and Tanguay, R. M., Nature, 281, 501–503 (1979).
8. Bowen, I. B. R. and Flynn, I. W., In: Biology of the Kinetoplastida 1; W. H. R. Lumsden and D. E. Evans, eds. (London: Academic press) pp. 435–476, (1976).
9. Hoare, C. A., In: The African Trypanosomiasis; H. W. Mulligan ed. (Wiley Interscience. John Wiley and Sons, Inc. New York) pp. 3–59 (1970).
10. Hajduk, S. L., J. Protozool., 31, 41–47 (1984).
11. Killick-Kendrick, R., In: Biology of the Kinetoplastida, 2; W. H. R. Lumsden and D. E. Evans, eds (London Academic press) pp. 394–460 (1976).
12. Glasgow, J. P., In: The African Trypanosomiasis; H. W. Mulligan ed. (Wiley-Interscience. John Wiley and Sons, Inc., New York) pp. 348–381 (1970).
13. Ingolia, T. D. and Craig, E., Proc. Natl. Acad. Sci. USA, 79, 525–529 (1982).
14. Holmgren, R., Livak, K., Morimoto, R., Freund R. and Meselson, M., Cell, 18, 1359–1370 (1979).
15. Ingolia, T. D., Slater, M. R. and Graig, E. A., Mol. Cell Biol., 1388–1398 (1982).
16. Howard, J. G., Hale, C. and Ling, W., Parasite Immunology, 2, 303–314 (1980).
17. Landfear, S. M. and Wirth, D. F., Nature, 309, 716–717, (1984).
18. Behnel, J. and Rensing, L., Exptl. Cell Res., 91, 119–124 (1975).
19. Leenders, H. J. and Berendes, H. D., Chromosoma, 37, 433–444, (1972).
20. Hirumi, H., Doyle, J. J. and Hirumi, K., Science, 196, 992–994 (1976).
21. Cross, G. A. M., Parasitol., 71, 393–417 (1975).
22. Giannini, S. H., Trans. Roy. Soc. Trop. Med. Hyg., in press (1985).
23. Van der Ploeg, L. H. T., Valerio, D., De Lange, T., Bernards, A., Borst, P. and Grosveld, F.G., Nucl. Acid Res., 5905–5923 (1982).
24. Overath, P., Czichos, J., Stock, U. and Nonnengaesser, C., EMBO J. 2, 1721 (1983).
25. Van der Ploeg, L. H. T., Liu, A. Y. C., Michels, P. A. M., De Lange, T., Borst, P., Majumder, H. K., Weber, H., Veeneman G. H. and Van Boom, J., Nucl. Acids Res., 10, 3591–3604 (1982).
26. Lehrach, H., Diamond, D., Wozney, J. M. and Boedtker, H., Biochemistry, 16, 4743 (1977).
27. Thomashow, L.S., Milhausen, M., Rutter, W. J. and Agabian, N., Cell, 32, 35–43 (1983).
28. Saraiva, E. M. B., Pimenta, P. F. P., Periera, M. E. A. and Der Souza, W., J. Parasitol, 69, 627–629 (1983).
9. Pan, A. A., Exptl. Parasitol., 58, 72–80 (1984).

What is claimed is:

1. A method for identifying in vitro whether a parasitic protozoan is a mammalian-infective form of the parasitic protozoan which comprises recovering total mRNA from the parasitic protozoan to be identified and detecting in the mRNA so recovered the presence of a mRNA transcript encoding a heat shock protein associated with the mammalian-infective form of the parasitic protozoan, which transcript is present only in the mammalian-infective form of the parasitic protozoan, wherein the detecting involves contacting the total mRNA recovered from the parasitic protozoan to be identified under hybridizing conditions with a detectable oligonucleotide which is complementary to at least a portion of the mRNA transcript which encodes the heat shock protein associated with the mammalian-infective form of the parasitic protozoan and detecting the formation of hybridization complexes between the mRNA transcript and the detectable oligonucleotide and thereby identifying in vitro the parasitic protozoan as the mammalian-infective parasitic form of the parasitic protozoan.

2. A method of claim 1, wherein prior to recovering mRNA from the protozoan, the protozoan is subjected in vitro to a temperature of about 37° C. for a sufficient time to cause the protozoan to differentiate to the mammalian-infective form.

3. A method of claim 1, wherein the parasitic protozoan is of the genus Leishmania or the genus Trypanosoma.

4. A method of claim 3, wherein the protozoan is *Leishmania tropica major*.

5. A method of claim 3, wherein the protozoan is *Leishmania brasiliensis*.

6. A method of claim 3, wherein the protozoan is *Leishmania peruviana*.

7. A method of claim 3, wherein the protozoan is *Leishmania mexicana*.

8. A method of claim 3, wherein the protozoan is *Leishmania donovani*.

9. A method of claim 3, wherein the protozoan is *Leishmania chagasi*.

10. A method of claim 3, wherein the protozoan is *Leishmania enriettii*.

11. A method of claim 3, wherein the protozoan is *Leishmania hertigi*.

12. A method of claim 3, wherein the protozoan is *Leishmania adleri*.

13. A method of claim 3, wherein the protozoan is *Trypanosoma brucei*.

14. A method of claim 3, wherein the protozoan is *Trypanosoma gambiense*.

15. A method of claim 3, wherein the protozoan is *Trypanosoma rhodesiense*.

16. A method of claim 3, wherein the protozoan is *Trypanosoma lewisi*.

17. A method of claim 3, wherein the protozoan is *Trypanosoma rangeli*.

18. A method of claim 1, wherein the parasitic protozoan is of the genus Coccidia, Babesia, Theileria, Plasmodium or Giardia.

19. A method of claim 1, wherein the detectable oligonucleotide comprises at least a portion of the DNA from Drosophila which encodes a Drosophila heat shock protein.

20. A method of claim 19, wherein the detectable oligonucleotide comprises at least a portion of the Drosophila heat shock gene Hsp 83.

21. A method of claim 19, wherein the detectable oligonucleotide comprises at least a portion of the Drosophila heat shock gene Hsp 70.

22. A method of claim 19, wherein the detectable oligonucleotide is radioactively labeled.

23. A method of claim 19, wherein the detection of the formation of hybridization complexes comprises gel electrophoresis.

24. A method of claim 19, wherein the detection of the formation of hybridization complexes comprises defective radioactive decay in a scintillation counter.

25. A method for identifying whether an agent is capable of blocking the formation of a mammalian-infective form of a parasitic protozoan which comprises in vitro subjecting a non-infective form of the parasitic protozoan in the presence of different amounts of the agent to be identified to a temperature of about 37° C. for a sufficient time to cause the parasitic protozoan to differentiate to the mammalian-infective form, recovering total mRNA from the resulting differentiated parasitic protozoan and detecting in the mRNA so recovered a mRNA transcript encoding a heat shock protein associated with the mammalian-infective form of the parasitic protozoan, which transcript is present only in the mammalian-infective form of the parasitic protozoan, wherein the detection involves contacting the total mRNA recovered from the parasitic protozoan under hybridizing conditions with a detectable oligonucleotide which is complementary to at least a portion of the mRNA transcript which encodes the heat shock protein associated with the mammalian-infective form of the parasitic protozoan and detecting the formation of hybridization complexes between the mRNA transcript and the detectable oligonucleotide and thereby the presence of the mRNA transcript encoding the heat shock protein associated with the mammalian-infective form of the parasitic protozoan, the absence of such mRNA transcript indicating that the agent has blocked the formation of the mammalian-infective form of the parasitic protozoan so as to thereby identify the agent as being capable of blocking the formation of the mammalian-infective form of the parasitic protozoan.

26. A method of claim 25 wherein the protozoan is of the genus Leishmania, Trypanosoma, Coccidia, Babesia, Theileria, Plasmodium or Giardia.

27. A method of claim 35, wherein the detectable oligonucleotide comprises at least a portion of the DNA from Drosophila which encodes a Drosophila heat shock protein.

28. A method of claim 27, wherein the detectable oligonucleotide comprises at least a portion of the Drosophila heat shock gene Hsp 83.

29. A method of claim 27, wherein the detectable oligonucleotide comprises at least a portion of the Drosophila heat shock gene Hsp 70.

30. A method of claim 25, wherein the detectable oligonucleotide is radioactively labeled.

31. A method of claim 25, wherein the detection of the formation of hybridization complexes comprises gel electrophoresis.

32. A method of claim 25, wherein the detection of the formation of hybridization complexes comprises detecting radioactive decay in a scintillation counter.

33. A method for identifying whether an agent is capable of blocking the formation of a mammalian-infective form of a parasitic protozoan which comprises in vitro subjecting a non-infective form of the parasitic protozoan in the presence of different amounts of the agent to be identified to a temperature of about 37° for a sufficient time to cause the parasitic protozoan to differentiate to the mammalian-infective form, recovering total mRNA from the resulting differentiated parasitic protozoan and quantitatively determining in the mRNA so recovered a mRNA transcript encoding a heat shock protein associated with the mammalian-infective form of the parasitic protozoan, which transcript is increased in numbers only in the mammalian-infective form of the parasitic protozoan, wherein the quantitative determination involves contacting the total mRNA recovered from the parasitic protozoan under hybridizing conditions with a detectable oligonucleotide which is complementary to at least a portion of the mRNA transcript which encodes the heat shock protein associated with the mammalian-infective form of the parasitic protozoan and detecting the formation of hybridization complexes between the mRNA transcript and the detectable oligonucleotide and thereby the increase in number of the mRNA transcript encoding the heat shock protein associated with the mammalian-infective form of the parasitic protozoan, the absence of an increase in the number of the mRNA transcript indicating that the agent has blocked the formation of the mammalian-infective form so as to thereby identify the agent as capable of blocking the formation of a mammalian-infective form of the parasite protozoan.

34. A method of claim 33 wherein the protozoan is of the genus Leishmania, Trypanosoma, Coccidia, Babesia, Theileria, Plasmodium or Giardia.

35. A method of claim 33, wherein the detectable oligonucleotide comprises at least a portion of the DNA from Drosophila which encodes a Drosophila heat shock protein.

36. A method of claim 35, wherein the detectable oligonucleotide comprises at least a portion of the Drosophila heat shock gene Hsp 83.

37. A method of claim 35, wherein the detectable oligonucleotide comprises at least a portion of thee Drosophila heat shock gene Hsp 70.

38. A method of claim 33, wherein the detectable oligonucleotide is radioactively labeled.

39. A method of claim 33, wherein the quantitative determination of the formation of hybridization complexes comprises gel electrophoresis.

40. A method of claim 33, wherein the quantitative determination of the formation of hybridization complexes comprises quantitatively determining radioactive decay in a scintillation counter.

41. A method for identifying in vitro whether a parasitic protozoan is a mammalian-infective form of the parasitic protozoan which comprises recovering total mRNA from the parasitic protozoan to be identified and quantitatively determining in the mRNA so recovered the number of mRNA transcripts encoding a heat shock protein associated with the mammalian-infective form of the parasitic protozoan, which transcripts are present in increased numbers only in the mammalian-infective form of the parasitic protozoan, wherein the quantitative determination involves contacting the total mRNA recovered from the parasitic protozoan under hybridizing conditions with a detectable oligonucleotide which is complementary to at least a portion of the mRNA transcripts which encode the heat shock protein associated with the mammalian-infective form of the parasitic protozoan and quantitatively determining the formation of hybridization complexes between the mRNA transcripts and the detectable oligonucleotide and thereby the increase in number of mRNA transcripts encoding the heat shock protein associated with the mammalian-infective form of the parasitic protozoan and thus identifying in vitro the parasitic protozoan as the mammalian-infective form of the parasitic protozoan.

42. A method of claim 41, wherein the detectable oligonucleotide comprises at least a portion of the DNA from Drosophila which encodes a Drosophila heat shock protein.

43. A method of claim 42, wherein the detectable oligonucleotide comprises at least a portion of the Drosophila heat shock gene Hsp 83.

44. A method of claim 42, wherein the detectable oligonucleotide comprises at least a portion of the Drosophila heat shock gene Hsp 70.

45. A method of claim 41, wherein the detectable oligonucleotide is radioactively labeled.

46. A method of claim 41, wherein the quantitative determination of the formation of hybridization complexes comprises gel electrophoresis.

47. A method of claim 41, wherein the quantitative determination of the formation of hybridization complexes comprises quantitatively determining radioactive decay in a scintillation counter.

48. A method of claim 41, wherein prior to recovering mRNA from the protozoan, the protozoan is subjected in vitro to a temperature of about 37° C. for a sufficient time to cause the protozoan to differentiate to the mammalian-infective form.

* * * * *